(12) United States Patent
Krull et al.

(10) Patent No.: US 12,205,714 B1
(45) Date of Patent: Jan. 21, 2025

(54) MEDICATION INVENTORY SYSTEM INCLUDING BOUNDING BOX IMAGE CAPTURE AND RELATED METHODS

(71) Applicant: Inmar Rx Solutions, Inc., Ft. Worth, TX (US)

(72) Inventors: Justin A. Krull, Weirton, WV (US); James W. McCracken, Jr., Lewisville, NC (US)

(73) Assignee: INMAR RX SOLUTIONS, INC., Ft. Worth, TX (US)

(*) Notice: Subject to any disclaimer, the term of this patent is extended or adjusted under 35 U.S.C. 154(b) by 320 days.

(21) Appl. No.: 17/832,442

(22) Filed: Jun. 3, 2022

(51) Int. Cl.
*G16H 40/20* (2018.01)

(52) U.S. Cl.
CPC .................. *G16H 40/20* (2018.01)

(58) Field of Classification Search
CPC .. G06Q 10/087; G06Q 20/3276; G16H 20/13; G16H 20/10; A61J 7/0084; A61J 2205/10; A61J 1/035; A61J 7/0069; A61J 1/03; G06T 7/30; G06T 3/18; G06T 7/20
See application file for complete search history.

(56) References Cited

U.S. PATENT DOCUMENTS

| | | | | |
|---|---|---|---|---|
| 11,227,446 | B2* | 1/2022 | Malia | H04L 12/2803 |
| 2016/0364686 | A1* | 12/2016 | Wolfe | G16H 30/40 |
| 2017/0246083 | A1 | 8/2017 | Amano et al. | |
| 2017/0270508 | A1 | 9/2017 | Roach et al. | |
| 2018/0198984 | A1* | 7/2018 | Palma | H04N 5/272 |
| 2018/0260665 | A1* | 9/2018 | Zhang | G06F 18/22 |
| 2020/0226545 | A1* | 7/2020 | Reid | G06K 7/10861 |
| 2021/0304122 | A1* | 9/2021 | Dattamajumdar | G16H 40/20 |
| 2021/0304862 | A1* | 9/2021 | Moreno | G16H 40/67 |
| 2022/0207479 | A1* | 6/2022 | Reid | G06K 7/1417 |
| 2022/0238200 | A1* | 7/2022 | Barbier | A61J 1/03 |

OTHER PUBLICATIONS

Rogers et al., U.S. Appl. No. 17/217,991, filed Mar. 30, 2021, (cited Utility Application is stored in the USPTO's Pair IFW system).

* cited by examiner

*Primary Examiner* — Florian M Zeender
*Assistant Examiner* — Vanessa Deligi
(74) *Attorney, Agent, or Firm* — ALLEN, DYER, DOPPELT, GILCHRIST, P.A.

(57) ABSTRACT

A medication inventory system may include a medication tray that includes compartments for storing respective medications. The medication tray may include a boundary wall defining a boundary outline of the medication tray, and the medication tray may have a tray identifier associated therewith. The medication inventory system may also include a user device that includes a housing, a camera carried by the housing, a display carried by the housing, and a controller coupled to the camera and the display. The controller may generate on the display a bounding box overlay image on a live image from the camera of the medication tray, capture an image from the camera when the bounding box overlay image is aligned relative to the boundary outline of the medication tray. The controller may also generate a current medication stocking list of the medication tray based upon the captured image and the tray identifier.

18 Claims, 8 Drawing Sheets

MEDICATION INVENTORY SYSTEM INCLUDING BOUNDING BOX IMAGE CAPTURE AND RELATED METHODS

TECHNICAL FIELD

The present invention relates to the field of medicine, and, more particularly, to medication inventory systems and related methods.

BACKGROUND

Medications, including controlled substances, medical devices, and/or medical tools may be relatively important for treatment of a patient. Thus, it may be desirable to maintain medications in a relatively orderly and predictable fashion to reduce the amount of time it takes to access these medications, particularly in a time sensitive situation.

A medication tray is often used to provide a specific selection and quantity of medications for a particular medical use case, physician preference, and/or location. A given health care facility may have multiple variations of medication trays in use, each varying in type, amount, and/or placement of medications within the medication tray. Multiple medication trays may be used within a crash cart, which is a wheeled cart for dispensing of medication (e.g., in an emergency). Consequently, health care facility pharmacies may process and manage a relatively large quantity of medication trays used throughout a facility.

Accordingly, the medication trays are typically managed. Contents of the medication trays may be replenished and verified, for example, between uses. The verification may be performed manually and include inspection for recalled, expired, and misplaced medications.

U.S. Patent Application Publication No. 2017/0246083 to Amano et al. is directed to a medicine sorting apparatus. More particularly, Amano et al. discloses a medicine sorting apparatus that includes an identifying part, e.g., based upon a camera, which can identify a direction, a posture and characteristics such as a shape, a size, a type and an expiration date of a medicine, and a storing part for storing the medicine so that the medicine can be taken from the storing part. A determination processing part can determine whether or not the medicine is a target to be treated based on the characteristics of the medicine identified by the identifying part.

U.S. Patent Application Publication No. 2018/0260665 to Zhang et al. is directed to a deep learning system for recognizing pills in images. More particularly, the system and method use deep learning, including convolutional neural networks, to identify subject objects in unconstrained user images such as unknown pills. An image of, e.g., a pill, may be captured and subsequently processed using deep learning models to identify the pill. The deep learning models may be optimized to have a small footprint (in terms of computational and memory resources) suitable for a resource-limited device such as a smartphone while retaining a high object recognition accuracy. Each such model may also be run on modified versions of the unconstrained image, for example on color, greyscale, and gradient images, to focus the models on different distinguishing features of the object.

SUMMARY

A medication inventory system may include a medication tray including a plurality of compartments for storing respective medications. The medication tray may include a boundary wall defining a boundary outline of the medication tray, and the medication tray having a tray identifier associated therewith. The medication inventory system may also include a user device that includes a housing, a camera carried by the housing, a display carried by the housing, and a controller coupled to the camera and the display. The controller may be configured to generate on the display a bounding box overlay image on a live image from the camera of the medication tray, and capture an image from the camera when the bounding box overlay image is aligned relative to the boundary outline of the medication tray. The controller may further be configured to generate a current medication stocking list of the medication tray based upon the captured image and the tray identifier.

The user device may include an orientation sensor carried by the housing. The controller may be configured to cooperate with the orientation sensor to determine an orientation of the user device and generate the bounding box overlay image based upon the orientation of the user device, for example.

The controller may be configured to change a shape of the bounding box overlay image based upon the orientation of the housing. The orientation sensor may include one of a gyroscope and an accelerometer, for example.

The controller may be configured to identify the boundary outline of the medication tray based upon the tray identifier and the captured image of the medication tray. The medication inventory system may include a plurality of boundary markers carried by the boundary wall, and the controller may be configured to apply an edge detection algorithm to the captured image to identify the boundary outline of the medication tray based upon the plurality of boundary markers, for example.

The controller may be configured to determine an amount of pixels of at least one of the medications and the tray identifier, and generate the bounding box overlay image based upon the determined amount of pixels. The controller may be configured to determine a desired medication stocking list for the medication tray based upon the tray identifier. The controller may be configured to determine at least one missing medication based upon the current medication stocking list and the desired medication stocking list, for example.

A method aspect is directed to a method of processing medication inventory in a medication inventory system that includes a medication tray including a plurality of compartments for storing respective medications. The medication tray may include a boundary wall defining a boundary outline of the medication tray, and the medication tray may have a tray identifier associated therewith. The method may include using a user device including a housing, a camera carried by the housing, and a display carried by the housing to generate on the display a bounding box overlay image on a live image from the camera of the medication tray, and capture an image from the camera when the bounding box overlay image is aligned relative to the boundary outline of the medication tray. The method may also include using the user device to generate a current medication stocking list of the medication tray based upon the captured image and the tray identifier.

A computer readable medium aspect is directed to a non-transitory computer readable medium for processing medication inventory. The non-transitory computer readable medium includes computer executable instructions that when executed by a controller of a user device cause the controller to perform operations. The operations may include generating, on a display of the user device, a bounding box overlay image on a live image from a camera of the user device of a medication tray. The medication tray may include a plurality of compartments for storing respective medications, and a boundary wall defining a boundary outline of the medication tray, and the medication tray may have a tray identifier associated therewith. The operations may also include capturing an image from the camera of the user device when the bounding box overlay image is aligned relative to the boundary outline of the medication tray, and generating a current medication stocking list of the medication tray based upon the captured image and the tray identifier.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1:
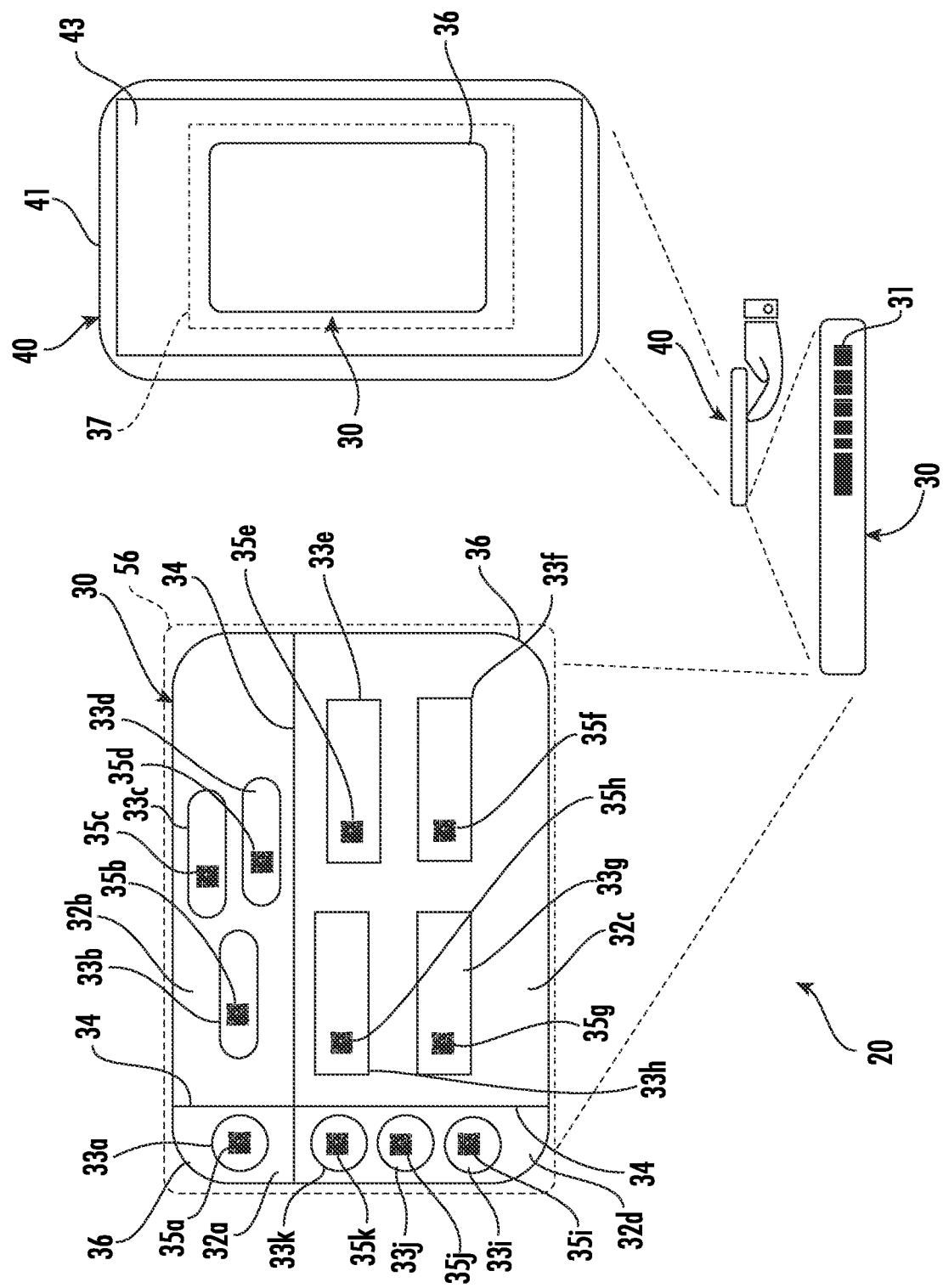
FIG. 1 is a schematic diagram of a medication inventory system in accordance with an embodiment.

Referring initially to FIG. 1, a medication inventory system 20 includes a medication tray 30 that includes compartments 32a-32n, defined by partitions 34, for storing respective medications 33a-33n. Each compartment may store a medication 33a-33n, multiple medications, a medical or medicated device, a medication container that includes individual medications therein, or other item or substance used for medical treatment. For example, the medication tray 30 may be part of a crash cart, as will be appreciated by those skilled in the art. Of course, the medication tray 30 may be used in other medical environments, for example, an examination room, emergency room, treatment room, operating room, etc. For example, the medication tray 30 may be in the form of a drawer within a medication cabinet or medication dispensing cabinet. Each medication 33a-33n has a respective medication identifier 35a-35n associated therewith, for example, a barcode, quick-response (QR) code, alphanumeric characters, or other optically recognizable and unique code.

The medication tray 30 includes a boundary wall 36 that defines a boundary outline 56 of the medication tray. More particularly, the boundary wall 36 includes first and second opposing perimeter walls that define the boundary outline. In some embodiments, for example, where the medication tray 30 has a round shape, there may be only a single boundary wall 36.

The medication tray 30 has a tray identifier 31 associated therewith. The tray identifier 31 may be in the form of a barcode, for example, that may be printed or applied (e.g., via an adhesive label) on the medication tray 30. The tray identifier 31 may be in the form of another type of identifier, for example, QR code, alphanumeric characters, or other optically recognizable and unique code.

Figure 2:
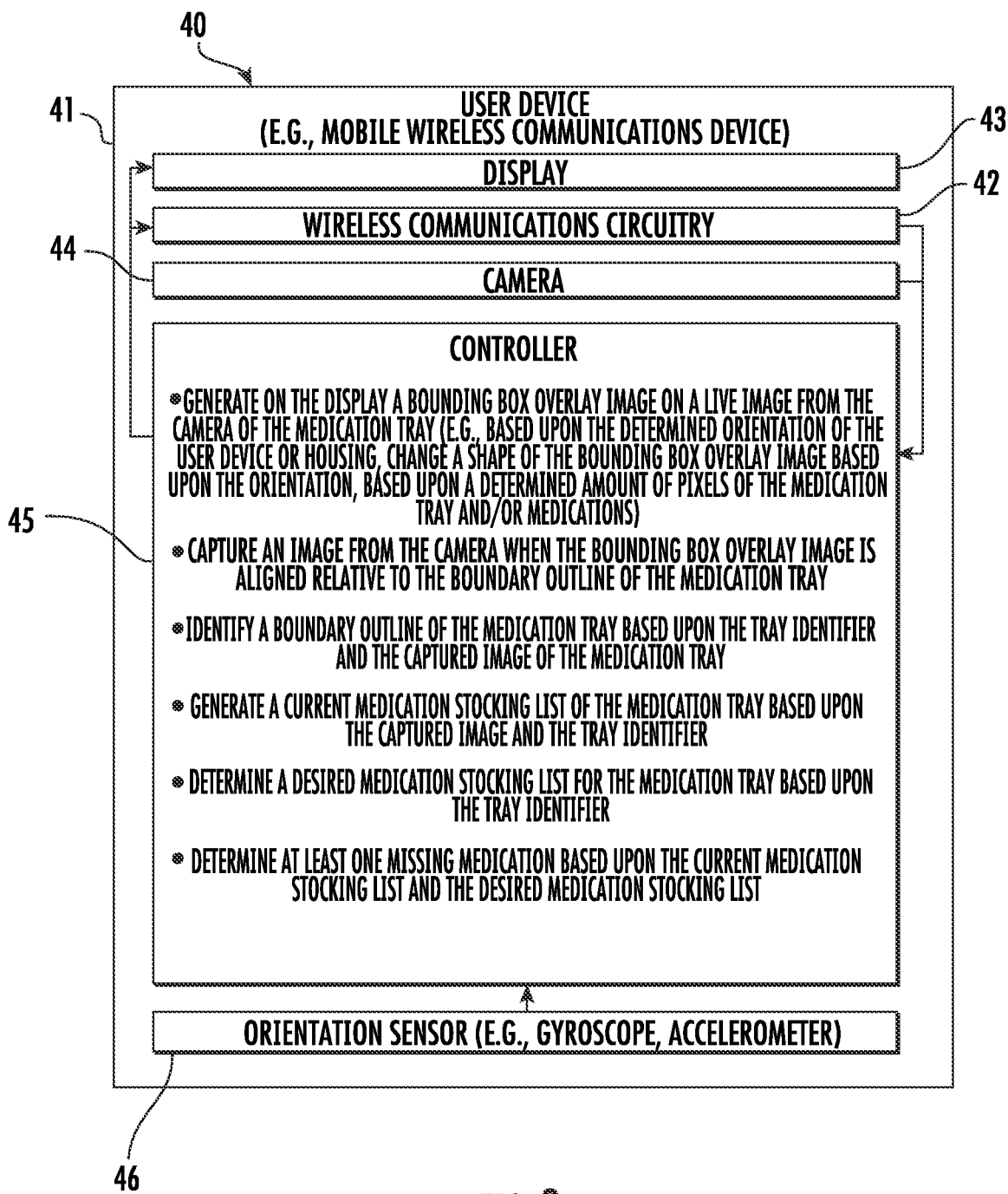
FIG. 2 is a schematic block diagram of the user device of FIG. 1.

Referring additionally to FIG. 2, the medication inventory system 20 also includes a user device that is illustratively in the form of a mobile wireless communications device 40 or smartphone. The mobile wireless communications device 40 illustratively includes a housing 41 and wireless communications circuitry 42 carried by the housing. The mobile wireless communications device 40 also includes a display 43, for example, a touch display, carried by the housing 41. A controller 45 is coupled to the wireless communications circuitry 42 and the display 43. A camera 44 is also carried by the housing 41 and coupled to the controller 45. One or more input devices may be carried by the housing 41 and coupled to the controller 45.

The mobile wireless communications device 40 may also include an orientation sensor 46. The orientation sensor 46 may be carried by the housing 41 and coupled to the controller 45. The orientation sensor 46 may include or be in the form of a gyroscope or accelerometer, for example. While the user device 40 is illustratively in the form of a mobile wireless communications device, the user device may be in the form of a tablet, laptop computer, or wearable device, for example.

Figure 3:
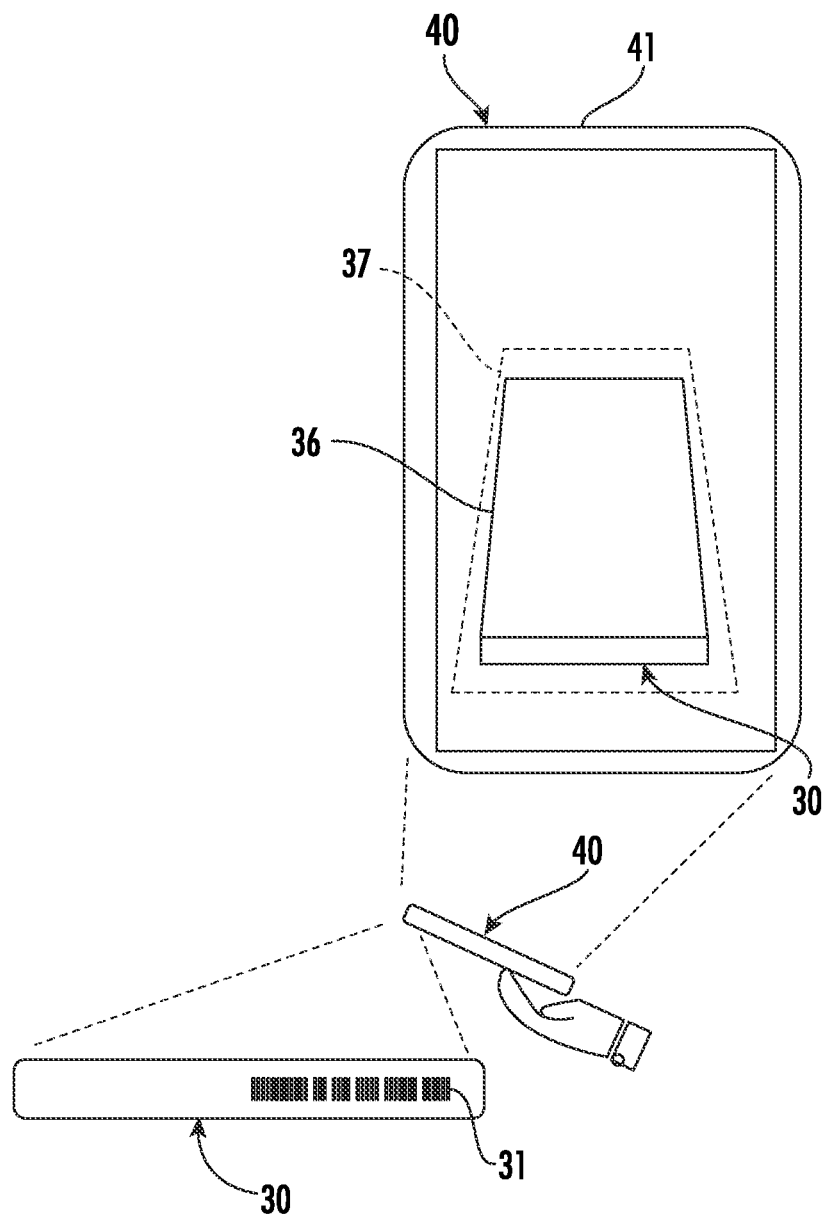
FIG. 3 is a schematic diagram of a portion of medication inventory system of FIG. 1 illustrating changing the shape of the bounding box overlay image.
Figure 4:
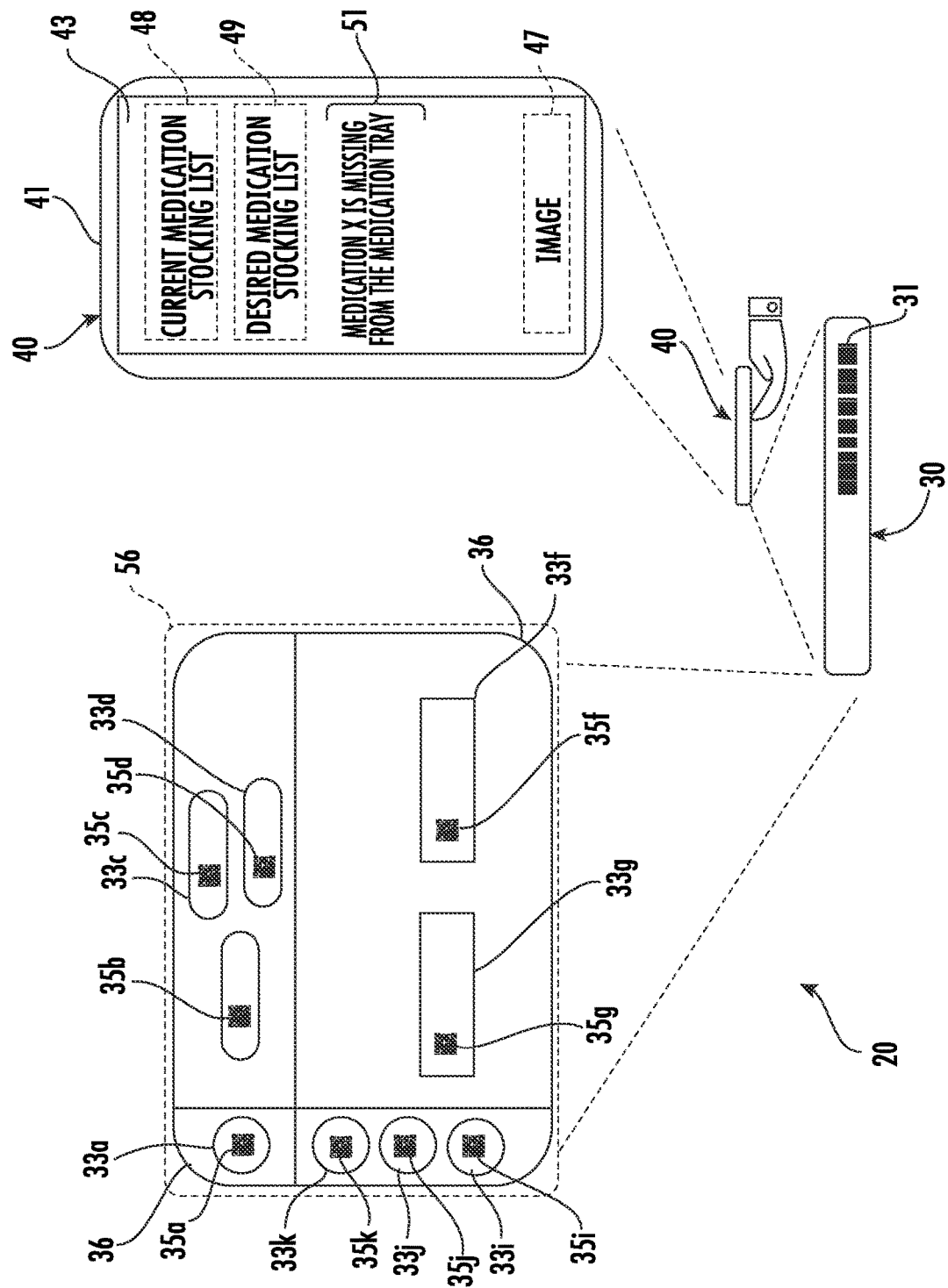
FIG. 4 is another schematic diagram of the medication inventory system of FIG. 1.
Figure 5:
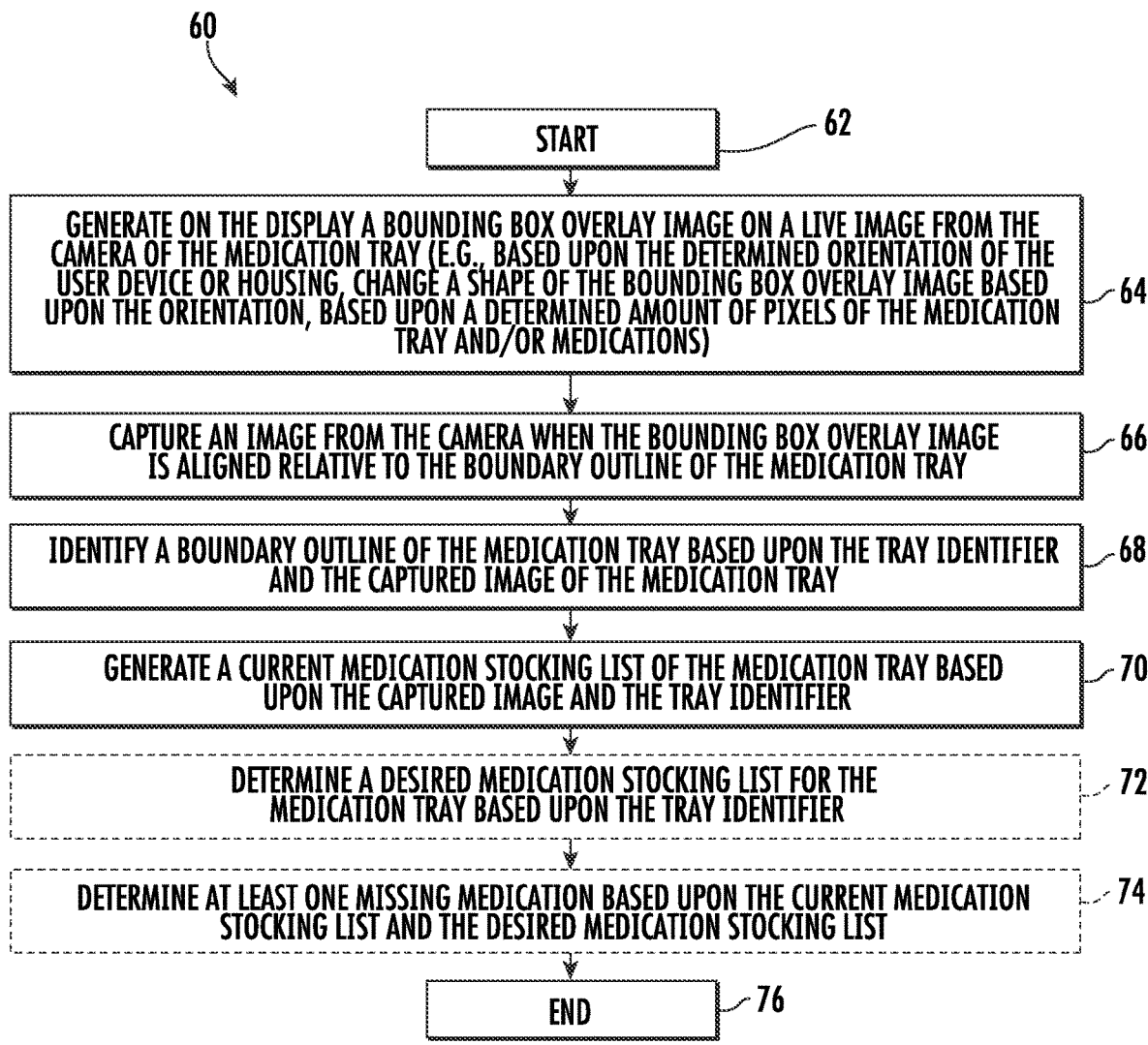
FIG. 5 is a flow diagram illustrating operation of the user device of FIG. 1.

Referring now additionally to FIGS. 3-4 and the flowchart 60 in FIG. 5, beginning at Block 62, operations of the user device 40 of the medication inventory system 20 will now be described. While operations of the user device 40 are described, it will be appreciated by those skilled in the art that the controller 45 and an associated memory cooperate to perform the operations.

At Block 64 the user device 40 generates, on the display 43, a bounding box overlay image 37 on a live image from the camera 44 of the medication tray 30 (FIG. 1). More particularly, the controller 45 may cooperate with the orientation sensor 46 to determine an orientation of the user device 40, and generates the bounding box overlay image 37 based upon the orientation of the user device (FIG. 3). As will be appreciated by those skilled in the art, the controller 45 changes the shape of the bounding box overlay image 37 based upon the orientation of the housing 41, for example, when the housing is held at a smaller angle relative to the medication tray 30, the bounding box overlay image 37 may change its shape and size to accommodate the change in overall site picture (FIG. 3). The controller 45 may calculate the shape of the bounding box overlay image 37, for example, to have a rectangular shape or a trapezoidal shape, depending on the orientation of the user device 40 relative to the medication tray 30. The bounding box overlay image 37 may be transparent or semi-transparent, and/or have fill or no fill.

The controller 45 may determine an amount of pixels of one or more of the medications 33a-33n and the tray identifier 31, and generate the bounding box overlay image 37 based upon the amount of pixels. In other words, the controller 45 may, for example, identify a size of a medication 33a-33n based upon an associated identifier or barcode. Thus, the amount of camera pixels represented can be calculated by the controller 45, for example, in a specific measurement (e.g., inches, centimeters). The calculated barcode size or medication size is compared to a known medication tray size (e.g., based upon the tray identifier 31 and in the x-, y-, or z-axes).

The user device 40, at Block 66, captures an image 47 from the camera 44 when the bounding box overlay image 37 is aligned relative to the boundary outline 56 of the medication tray 30. More particularly, the user device 40 may capture the image 47 based upon user input to the user device or via the display 43 when the display is in the form of a touch display. In some embodiments, the controller 45 may capture the image 47 without user input (i.e., automatically capture) when the bounding box overlay image 37 is aligned, and, for example, when the user device 40 is held steady.

The controller 45 may, at Block 68, identify the boundary outline 56 of the medication tray 30 based upon the tray identifier 31 and the captured image 47 of the medication tray. More particularly, the controller 45 may apply one or more edge detection algorithms to identify the boundary outline 56 of the medication tray 30. Those skilled in the art will appreciate that the accuracy of edge detection algorithms or the identification of the boundary outline 56 may be increased and/or the computational intensity reduced based upon capturing an image from the camera 44 when the bounding box overlay image 37 is aligned.

In an embodiment, the controller 45 may alter the live image so that the image of medication tray 30 on the display 43 appears to be square or rectangle in shape regardless of the orientation of the user device 40. More particularly, based upon the orientation sensor 46, the controller 45 may show on the display an altered version of the live image (i.e., to be acquired image). By using the orientation sensor 46 and thus determining the relative angle at which the image is to be acquired, and based upon determining a size or elements in the image (e.g., based upon pixel measurement), the controller 45 may apply a transform to display the image as if the camera were nearly directly overhead the medication tray 30. The controller 45 may alternatively alter the captured image 47 for use in determining the boundary outline 56.

At Block 70, the user device 40, via the controller 45, generates a current medication stocking list 48 of the medication tray 30 based upon the captured image 47, and more particularly, the identified boundary outline 56, and the tray identifier 31 from the captured image (FIG. 4). Those skilled in the art will appreciate that by basing the current medication stocking list to be based upon the captured image 47 (which is based upon the aligned bounding box overlay image 37) and, for example, the boundary outline 56, a more accurate and quicker processing time to generate the current medication stocking list 48 may be obtained since the controller 45 may not process parts of the image outside the boundary outline.

A current medication stocking list 48, for example, may be determined based upon a homographic algorithm applied to a captured image 47 or images, which may be based upon respective locations of the medication identifiers 35a-35n. An exemplary homographic algorithm, contrary to conventional homographic algorithms, does not use feature extraction or k-nearest-neighbor matching to provide the feature matches, but uses the individually identifiable identifiers (e.g., barcodes) already present in the process to provide feature matches, and as a result creates relatively consistent repeatable homographic processed images.

The controller 45 may optionally determine a desired medication stocking list 49 of the medication tray 30 based upon the tray identifier 31 (Block 72) (FIG. 4). More particularly, the controller 45 may obtain the desired medication stocking list 49 from a remote computer or database based upon the tray identifier 31. In other words, the tray identifier 31 may be used as an index to retrieve or obtain the desired medication stocking list 49.

The controller 45, at Block 74, may optionally determine one or more missing medications 33e, 33h (e.g., that may have been used) based upon the current medication stocking list 48 and the desired medication stocking list 49 (FIG. 4). More particularly, if a medication 33a-33n that is part of the desired medication stocking list 49 is determined to not be in the current medication stocking list 48 (i.e., a medication was not found in the images 47), a notification 51 may be generated and displayed on the display 43 of the user device 40 and/or communicated. The notification 51 may be in the form of a list, for example, and/or an image of the medication tray with indicia (e.g. color-coded). The controller 45 may use image recognition techniques, for example, for identifying the medication identifiers 35a-35n, to determine missing medications. In some embodiments, the mobile wireless communications device 40 may determine that a medication is missing based upon there being less than a desired number (e.g., a threshold number) of medications in a given compartment. Operations end at Block 76.

Figure 6:
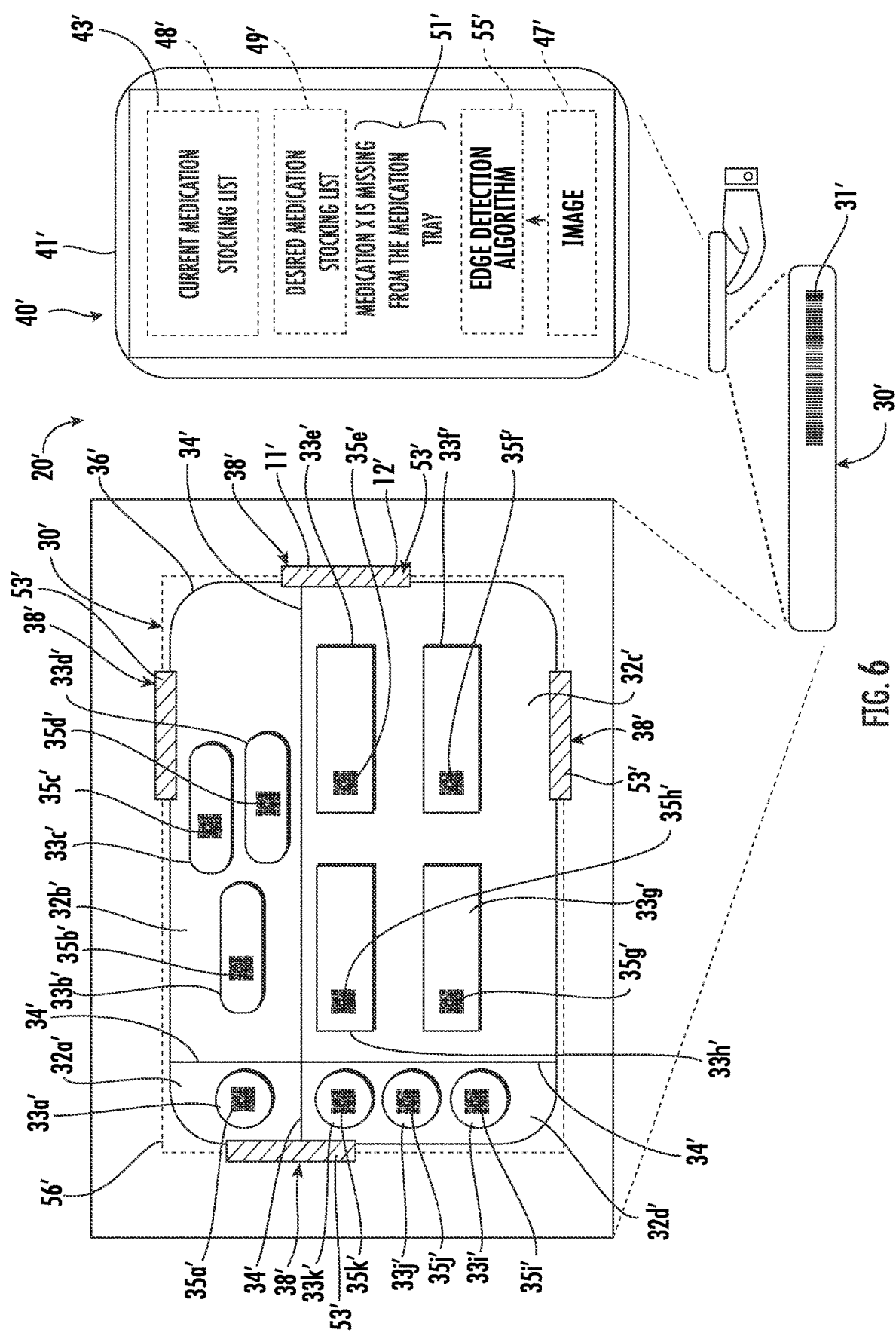
FIG. 6 is a schematic diagram of a medication inventory system in accordance with another embodiment.
Figure 7:
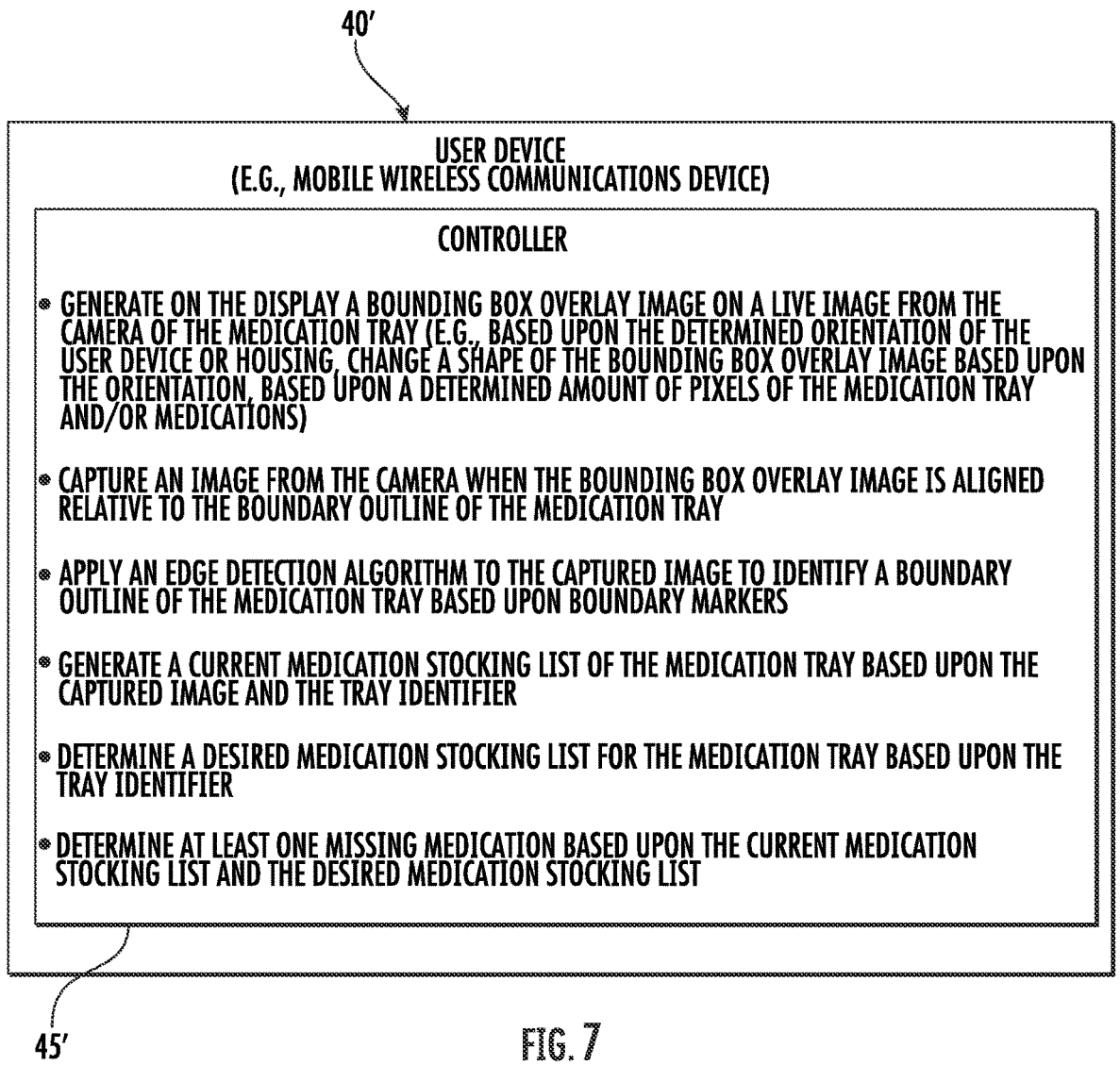
FIG. 7 is schematic block diagram of a portion of a user device of the medication inventory system of FIG. 6.
Figure 8:
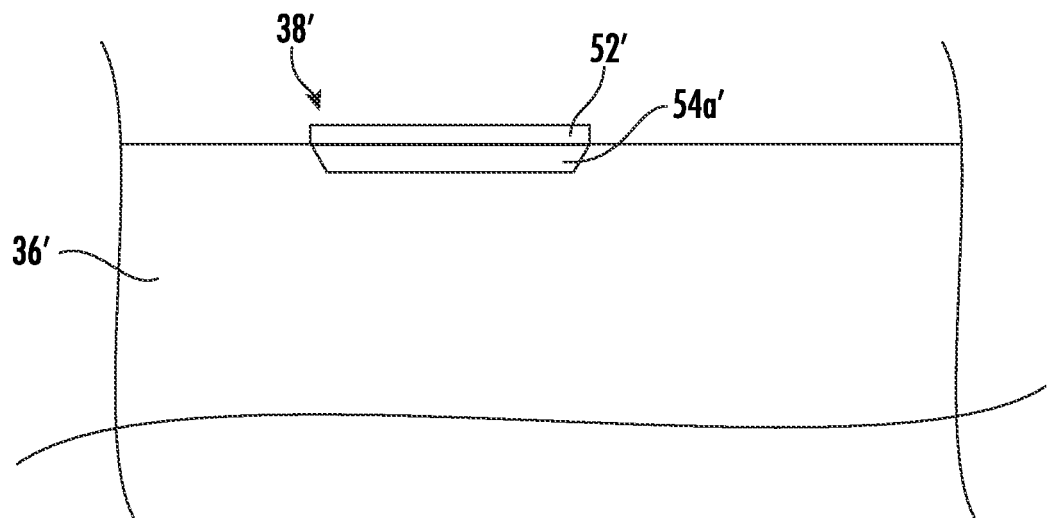
FIG. 8 is a schematic side view of a boundary marker in accordance with the medication inventory system of FIG. 6.
Figure 9:
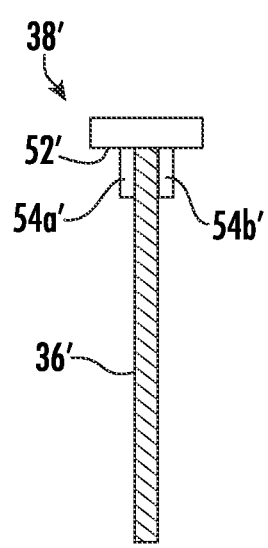
FIG. 9 is another schematic side view of a boundary marker in accordance with the medication inventory system of FIG. 6.

Referring now briefly to FIGS. 6-8, in an embodiment, the medication inventory system 20' also includes boundary markers 38' that are illustratively carried by the boundary wall 36'. Each boundary marker 38' includes a body 52' having a slot (e.g., a slotted based defined by two legs 54a', 54b') that is slidably positioned on the boundary wall 36'. On an upper surface of each boundary marker 38' is a machine readable indicia 53'. The indicia 53' may be in the form of an adhesive label or sticker having colored shapes thereon, different from the color of the boundary wall 36', that are detectable by a camera, for example, in a variety of lighting conditions and orientations. The upper surface of each boundary marker 38', which defines a top edge, is about 4 mm wide, which is sized to permit the machine readable indicia 53' to be shown along with a boundary region, for example, boundary "black" region. Of course, other types and sizes of coded boundary markers 38' may be used, for example, the sizing of which may be dependent on the algorithm used. The machine readable indicia 53' may include first and second color segments 11', 12', as will be described in further detail below.

In the present embodiment, the controller 45' applies an edge detection algorithm 55' to the captured image 47' to identify the boundary outline 56' of the medication tray 30' based upon the boundary markers 38'. The current medication stocking list 48' of the medication tray 30' may thus be generated based upon the identified boundary outline 56' using the boundary markers 38' or edge clips, and the tray identifier 31' from the captured image 47'. More particularly, the controller 45' may determine a size of the boundary markers 38' in terms of pixels, for example, using the techniques described above with respect to determining an amount of pixels, and the sizes of the boundary markers may be compared to known sizes of a medication tray 30'.

Further details of identifying a boundary outline 56' using boundary markers 38' will now be described. The controller 45' may extract red, green, and blue (RGB) pixel data from the image 47'. The RGB pixel data is converted to hue saturation value (HSV) space. In other words, as will be appreciated by those skilled in the art, to detect the corners, the RGB pixel data from the camera is converted to HSV space to yield HSV converted RGB pixel data. In the hue channel, the value of each pixel corresponds to the color of the pixel.

The at least one image is segmented based upon the HSV space. More particularly, the HSV space is used to segment the at least one image into "blobs" of the appropriate color (e.g., teal and yellow). Edge detection techniques or an edge detection algorithm may be applied to the color segments to identify the boundary outline 56' of the medication tray 30'. More particularly, the edge detection algorithm may be applied to detect the edges of the "blobs." As will be appreciated by those skilled in the art, edge detection algorithms may include the Canny, Sobel, or Laplacian of Gaussian techniques. Other and/or additional techniques may be used for edge detection.

Contour tracing may be applied. These contours may be filtered so that the contours that can represent the boundary markers 38', and more particularly, the colored machine readable indicia 53'. The filtering may be based on a perimeter length of the medication tray 30', aspect, and an assumption about a ratio of the length of the machine readable indicia 53' to the overall size of the medication tray. A smallest rectangle that includes the contour of each "blob" is then computed.

Each machine readable indicia 53' or adhesive label may include relatively bright or vibrant colors, for example, that may be printed with a CMYK printing process. Each machine readable indicia 53' may further include first and second color segments. An angle may be between the first and second color segments, for example, so that the first and second color segments overlap. By overlapping the first and second segments, a smallest enclosing rectangle of each segment may thus overlap with its neighbor, as will be appreciated by those skilled in the art. Colors may be chosen to include a relatively wide black border so that segmented color blobs do not merge into any neighboring regions with similar colors. This may allow for a wide range of hues, saturations, and values to be included in the detected color segments, for example, yellow and teal.

With respect to yellow and teal (i.e., yellow and teal "blobs"), for each yellow rectangle any coincident teal rectangles are found. If any yellow rectangle has two or more bounding teal rectangles, the subset of one yellow and two teal rectangles that is closest to having their centers in a line is added to a list of candidate edges.

Any yellow rectangles that are bounded by only one teal rectangle are added to a list of secondary candidates, on the assumption that some teal rectangles may not be well detected. If the total number of primary candidate edges is less than four, then these secondary candidates are added to the primary candidates in combinations totaling exactly four candidates, until the first set of candidate edges found intersect within the boundaries of the overall image. If the total number of primary candidate edges is greater than four, or no set of four primary and secondary candidate edges is found that intersect within the image, then the image is rejected and the user may be directed to take the picture of the medication tray 30' from a different angle or with better lighting, for example.

For the final list of candidate edges, edge direction is detected by drawing a line between the center of the two bordering teal rectangles, or in the case of a yellow region with only one teal region bordering, drawing a line from the center of the yellow region to the center of the teal region. The corners are then computed by extending the lines of each edge and searching for intersection with other line edges.

Further refinement may be performed, for example, in the case where more than four candidates are found (either primary or combination of primary and secondary). The further refinement may include computing the set of corners for each potential set of four candidate edges, and using the set of corners closest to a rectangular area as the overall result.

While yellow and teal have been described herein with respect to the colors of the machine readable indicia 53', those skilled in the art will appreciate that other colors may be used. Additionally, where the medication tray 30' is sized so that each boundary marker 38' does not slidably position on the boundary wall 36', additional boundary marker and indicia templates may be used and may include a relatively flat upper surface that may point true at the corners coincident to the edge. With respect to drawers or cabinets, for example, the indicia 53' may be sized to be smaller than those used with the medication tray 30', and the boundary markers 38' may be applied to a visible inside wall, with the color region as close to the top of the wall as possible. In order to be visible, the indicia 53' may be applied to the outside rather than the inside of the drawer. Other elements illustrated, but not described, for example, the compartments 32a'-32n', defined by partitions 34', for storing respective medications 33a'-33n', the medication identifiers 35a'-35n', the display 43', the desired medication stocking list 49', and the notification 51', are similar to those described above.

A method aspect is directed to a method of processing medication inventory in a medication inventory system 20 that includes a medication tray 30 including a plurality of compartments 32a-32n for storing respective medications 33a-33n. The medication tray 30 includes a boundary wall 36 defining a boundary outline 56 of the medication tray, and the medication tray has a tray identifier 31 associated therewith. The method includes using a user device 40 including a housing 41, a camera 44 carried by the housing, and a display 43 carried by the housing to generate on the display a bounding box overlay image 37 on a live image from the camera of the medication tray 30, and capture an image from the camera when the bounding box overlay is aligned relative to the boundary outline 56 of the medication tray. The method also includes using the user device 40 to generate a current medication stocking list 48 of the medication tray 30 based upon the captured image 47 and the tray identifier 31.

A computer readable medium aspect is directed to a non-transitory computer readable medium for processing medication inventory. The non-transitory computer readable medium includes computer executable instructions that when executed by a controller 45 of a user device 40 cause the controller to perform operations. The operations include generating, on a display 43 of the user device 40, a bounding box overlay image 37 on a live image from a camera 44 of the user device of a medication tray 30. The medication tray 30 includes a plurality of compartments 32a-32n for storing respective medications 33a-33n, and a boundary wall 36 defining a boundary outline 56 of the medication tray 30, and the medication tray has a tray identifier 31 associated therewith. The operations also include capturing an image 47 from the camera 44 of the user device 40 when the bounding box overlay 37 is aligned relative to the boundary outline 56 of the medication tray 30, and generating a current medication stocking list 48 of the medication tray based upon the captured image and the tray identifier 31.

While several embodiments have been described herein, it should be appreciated by those skilled in the art that any element or elements from one or more embodiments may be used with any other element or elements from any other embodiment or embodiments. Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

The invention claimed is:

1. A medication inventory system comprising:
a medication tray comprising a plurality of compartments for storing respective medications, the medication tray comprising a boundary wall defining a boundary outline of the medication tray, and the medication tray having a tray identifier associated therewith; and
a user device comprising a housing, a camera carried by the housing, a display carried by the housing, an orientation sensor carried by the housing, and a controller coupled to the camera and the display, the controller configured to
determine an orientation of the user device relative to the medication tray based upon the orientation sensor,
determine an amount of pixels of at least one of the medications and the tray identifier from a live image from the camera of the medication tray,
apply a transform to the live image of the medication tray based upon the orientation of the user device and the amount of pixels of the at least one of the medications and the tray identifier so that the live image displayed as if the camera were overhead the medication tray,
display the transformed live image on the display,
generate on the display a bounding box overlay image on the transformed live image from the camera of the medication tray based upon the orientation of the user device,
capture an image from the camera when the bounding box overlay image is aligned relative to the boundary outline of the medication tray, and
generate a current medication stocking list of the medication tray based upon the captured image and the tray identifier.

2. The medication inventory system of claim 1 wherein the controller is configured to change a shape of the bounding box overlay image based upon the orientation of the housing.

3. The medication inventory system of claim 1 wherein the orientation sensor comprises one of a gyroscope and an accelerometer.

4. The medication inventory system of claim 1 wherein the controller is configured to identify the boundary outline of the medication tray based upon the tray identifier and the captured image of the medication tray.

5. The medication inventory system of claim 4 comprising a plurality of boundary markers carried by the boundary wall; and wherein the controller is configured to apply an edge detection algorithm to the captured image to identify the boundary outline of the medication tray based upon the plurality of boundary markers.

6. The medication inventory system of claim 1 wherein the controller is configured to determine a desired medication stocking list for the medication tray based upon the tray identifier.

7. The medication inventory system of claim 6 wherein the controller is configured to determine at least one missing medication based upon the current medication stocking list and the desired medication stocking list.

8. A user device comprising:
a housing;
a camera carried by the housing;
a display carried by the housing;
an orientation sensor carried by the housing; and
a controller coupled to the camera, the display, and the orientation sensor, the controller configured to
determine an orientation of the user device relative to the medication tray based upon the orientation sensor,
determine an amount of pixels of at least one of the medications and the tray identifier from a live image from the camera of the medication tray,
apply a transform to the live image of the medication tray based upon the orientation of the user device and the amount of pixels of the at least one of the medications and the tray identifier so that the live image is displayed as if the camera were overhead the medication tray,
display the transformed live image on the display,
generate on the display a bounding box overlay image on the transformed live image from the camera of a medication tray based upon the orientation of the user device, the medication tray comprising a plurality of compartments for storing respective medications, and a boundary wall defining a boundary outline of the medication tray, and the medication tray having a tray identifier associated therewith,
capture an image from the camera when the bounding box overlay image is aligned relative to the boundary outline of the medication tray, and
generate a current medication stocking list of the medication tray based upon the captured image and the tray identifier.

9. The user device of claim 8, wherein the controller is configured to change a shape of the bounding box overlay image based upon the orientation of the housing.

10. The user device of claim 8 wherein the orientation sensor comprises one of a gyroscope and an accelerometer.

11. The user device of claim 8 wherein the controller is configured to identify the boundary outline of the medication tray based upon the tray identifier and the captured image of the medication tray.

12. A method of processing medication inventory in a medication inventory system comprising a medication tray comprising a plurality of compartments for storing respective medications, the medication tray comprising a boundary wall defining a boundary outline of the medication tray, and the medication tray having a tray identifier associated therewith, the method comprising:
using a user device comprising a housing, a camera carried by the housing, a display carried by the housing, and an orientation sensor carried by the housing to
determine an orientation of the user device relative to the medication tray based upon the orientation sensor, determine an amount of pixels of at least one of the medications and the tray identifier from a live image from the camera of the medication tray, apply a transform to the live image of the medication tray based upon the orientation of the user device and the amount of pixels of the at least one of the medications and the tray identifier so that the live image is displayed as if the camera were overhead the medication tray, display the transformed live image on the display, generate on the display a bounding box overlay image on the transformed live image from the camera of the medication tray based upon the orientation of the user device, capture an image from the camera when the bounding box overlay image is aligned relative to the boundary outline of the medication tray, and generate a current medication stocking list of the medication tray based upon the captured image and the tray identifier.

13. The method of claim 12 wherein using the user device comprises using the user device to change a shape of the bounding box image based upon the orientation of the housing.

14. The method of claim 12 wherein using the user device comprises using the user device to identify the boundary outline of the medication tray based upon the tray identifier and the captured image of the medication tray.

15. A non-transitory computer readable medium for processing medication inventory, the non-transitory computer readable medium comprising computer executable instructions that when executed by a controller of a user device cause the controller to perform operations comprising:

determining an orientation of the user device relative to a medication tray having a tray identifier associated therewith based upon an orientation sensor of the user device;

determining an amount of pixels of at least one medication stored in the medication tray and the tray identifier from a live image from a camera of the user device of the medication tray;

applying a transform to the live image of the medication tray based upon the orientation of the user device and the amount of pixels of the at least one medication stored within the medication tray and the tray identifier so that the live image is displayed as if the camera were overhead the medication tray;

displaying the transformed live image on a display of the user device;

generating, on the display of the user device, a bounding box overlay image on the transformed live image of a medication tray based upon the orientation of the user device, the medication tray comprising a plurality of compartments for storing respective ones of the medications, and a boundary wall defining a boundary outline of the medication tray;

capturing an image from the camera of the user device when the bounding box overlay image is aligned relative to the boundary outline of the medication tray; and generating a current medication stocking list of the medication tray based upon the captured image and the tray identifier.

16. The non-transitory computer readable medium of claim 15 wherein the operations comprise cooperating with an orientation sensor of the user device to determine an orientation of the user device and generate the bounding box overlay image based upon the orientation of the user device.

17. The non-transitory computer readable medium of claim 16 wherein the operations comprise changing a shape of the bounding box overlay image based upon the orientation of the housing.

18. The non-transitory computer readable medium of claim 15 wherein the operations comprise identifying boundary outline of the medication tray based upon the tray identifier and the captured image of the medication tray.

* * * * *